United States Patent
Yasuura et al.

(10) Patent No.: US 7,198,803 B2
(45) Date of Patent: Apr. 3, 2007

(54) SUSTAINED RELEASE ORAL PREPARATIONS

(75) Inventors: Hiroyuki Yasuura, Kusatsu (JP); Kenya Akada, Nagaokakyo (JP); Shogo Izumi, Kameoka (JP)

(73) Assignee: Nippon Shinyaku Co., Ltd., Kyoto (JP)

(*) Notice: Subject to any disclaimer, the term of this patent is extended or adjusted under 35 U.S.C. 154(b) by 359 days.

(21) Appl. No.: 10/221,425

(22) PCT Filed: Mar. 19, 2001

(86) PCT No.: PCT/JP01/02143

§ 371 (c)(1),
(2), (4) Date: Sep. 11, 2002

(87) PCT Pub. No.: WO01/70221

PCT Pub. Date: Sep. 27, 2001

(65) Prior Publication Data

US 2003/0044465 A1   Mar. 6, 2003

(30) Foreign Application Priority Data

Mar. 21, 2000   (JP) .................... 2000-078692

(51) Int. Cl.
*A61K 9/22*   (2006.01)
*A61K 31/40*   (2006.01)

(52) U.S. Cl. ...................... 424/468; 514/426

(58) Field of Classification Search ............. 424/422, 424/464, 468, 476, 494; 514/422, 426, 427

See application file for complete search history.

(56) References Cited

U.S. PATENT DOCUMENTS

| 5,688,510 | A | | 11/1997 | Nakamichi et al. |
| 5,998,459 | A | * | 12/1999 | Tsuda et al. ............... 514/408 |
| 6,143,328 | A | * | 11/2000 | Heafield et al. ............ 424/489 |
| 6,183,779 | B1 | * | 2/2001 | Ouali et al. ............... 424/472 |
| 6,353,016 | B1 | | 3/2002 | Tanaka et al. |
| 6,692,769 | B1 | * | 2/2004 | Ishibashi et al. .......... 424/490 |

FOREIGN PATENT DOCUMENTS

| EP | 0 729 748 A1 | | 9/1996 |
| EP | 0 842 923 A1 | | 5/1998 |
| EP | 1 057 485 A1 | * | 12/2000 |
| EP | 1057485 A1 | * | 12/2000 |

OTHER PUBLICATIONS

The Technology of Dosage Forms, Edited by T.S. Kondrat'eva, Moscow, Meditsina, 1991, vol. 1, pp. 106-108.
The Technology of Dosage Forms, Edited by L.A. Ivanova, Moscow, Meditsina, 1991, vol. 2, pp. 183-189.
The Japanese Pharmacopoeia, Thirteenth Edition, Official from Apr. 1, 1996, pp. 33-36.

* cited by examiner

*Primary Examiner*—Sharon Kennedy
(74) *Attorney, Agent, or Firm*—Greenberg Traurig, LLP; Gerard F. Diebner

(57) ABSTRACT

Medicinal preparations containing a drug 2-amino-3-cyano-5-2(2-fluorophenyl)-4-methylpyrrole wherein the QOL and compliance of patients taking this drug can be improved and an unnecessary increase in the drug concentration in the plasma can be prevented by sustaining the release speed of the drug in vivo and lowering the administration frequency of the drug. That is, sustained release oral preparations containing 2-amino-3-cyano-5-(2-fluorophenyl)-4-methylpyrrole as the active ingredient.

13 Claims, 2 Drawing Sheets

SUSTAINED RELEASE ORAL PREPARATIONS

REFERENCE TO RELATED APPLICATIONS

This application claims priority from application PCT/JP01/02143, filed Mar. 19, 2001, which claims priority from Japanese application 2000-78,692 filed Mar. 21, 2000.

TECHNICAL FIELD

The present invention relates to 2-amino-3-cyano-5-(2-fluorophenyl)-4-methylpyrrole having the following structure (I):

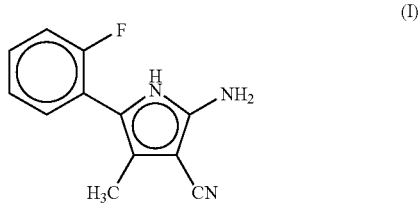

BACKGROUND ART

2-Amino-3-cyano-5-(2-fluorophenyl)-4-methylpyrrole is known to be an excellent therapeutic drug for treating pollakiuria and urinary incontinence having a bladder-selective calcium-sensitive potassium channel activating effect (see PCT WO99/36068).

On the other hand, the above described drug was found to have a short plasma half life, which may cause nocturnal pollakiuria or urinary incontinence, due to which a patient is forced to dose the drug at night, resulting in a problematic reduction in the QOL (quality of life) or the compliance of the patient.

DISCLOSURE OF THE INVENTION

An object of the present invention is to provide a pharmaceutical preparation containing the drug as an active ingredient, which is capable of improving the QOL and the compliance of the patient who doses the drug while avoiding any excessive increase in the plasma level of the drug by means of controlling the in vivo release rate of the drug and also by means of reducing the frequency of taking the drug.

In order to solve the above described problem, the present invention provides a controlled release oral preparation (hereinafter, referred to as "the preparation of the present invention") containing 2-amino-3-cyano-5-(2-fluorophenyl)-4-methylpyrrole (hereinafter, referred to as "the present compound") as an active ingredient.

The term "controlled release oral preparation" employed herein means an oral preparation with the release or dissolution (hereinafter, simply referred to as "release") of an active ingredient controlled. In the present invention, the dosage form or composition of the preparation is not limited particularly, as long as the preparation is a controlled release oral preparation having the above described functions.

A preparation which does not have the release controlling ability according to the present invention usually exhibits a release ratio of the drug 90% by weight or more within one hour, for example, when it is subjected to the dissolution test as directed in Method 2 under the 13th Japanese Pharmacopoeia which will be described later. The preparation of the present invention, when it is subjected to a similar test, exhibits a release ratio of the present compound, for example, of 0 to 70% by weight after 1 hour, 0 to 80% by weight after 2 hours, 5 to 95% by weight after 4 hours, 10 to 100% by weight after 8 hours, 20 to 100% by weight after 12 hours and 50 to 100% by weight after 24 hours, preferably, of 5 to 60% by weight after 1 hour, 10 to 70% by weight after 2 hours, 20 to 90% by weight after 4 hours, 30 to 100% by weight after 8 hours, 40 to 100% by weight after 12 hours and 50 to 100% by weight after 24 hours.

However, a preparation which releases the present compound in an intestinal tract due to its nature, such as an enteric-coated preparation, can be included in the preparations according to the present invention since it is controlled so that the present compound is released in the intestinal tract, although it does not exhibit the release ratio in the above described test.

Generally, a controlled release oral preparation can be classified into a delayed release oral preparation and a sustained release oral preparation, both of which are included in the present invention.

The "delayed release oral preparation" can be regarded as a controlled release oral preparation which is designed so that the migration of the preparation from stomach to small intestine is retarded or so that the release of the drug from the preparation is effective in a site in intestine rather than in stomach. A concrete example thereof may include an enteric-coated preparation.

The "sustained release oral preparation" can be generally regarded as a controlled release oral preparation which is designed so that the release of the drug from a preparation is effected gradually in a digestive tract regardless of whether it occurs in stomach or intestine. This sustained release type can be classified into a controlled release type intended to prolong the effect by maintaining a certain plasma level of the drug and a prolonged release type intended to prolong the effect without any ability of maintaining a certain plasma level of the drug, both of which are included in the present invention. Concrete examples of the sustained release oral preparation may include a sustained release film-coated preparation, SPAN-THRU preparation and wax matrix preparation.

The preparation of the present invention may employ only one of various controlled release means described above, or may be a combined oral preparation employing both of a delayed release oral preparation and a sustained release oral preparation. An instantaneous release property may also be combined partially.

A concrete preparation capable of exerting the above described release controlling ability, i.e., a concrete example of the preparation of the present invention may include any of those shown below which are known to those skilled in the art.

(1) Controlled Diffusion Oral Preparation

A controlled diffusion oral preparation is a preparation capable of controlling the release of a drug using a material which undergoes almost no dissolution in a fluid in a digestive tract, and examples thereof may be as follows, for example.

<1> Insoluble Film-coated Preparation

An insoluble film-coated preparation basically has a core containing a drug (the present compound) coated with a pharmaceutically acceptable material which undergoes almost no dissolution in a fluid in a digestive tract (insoluble material). Such an insoluble film-coated preparation can control the release of the drug (the present compound) from a preparation due to the barrier of the insoluble material present as a coating film thereon.

An example of the insoluble film-coated preparation according to the present invention may include a sustained release granule preparation or a sustained release film-coated preparation containing the present compound as an active ingredient. The present compound which exists in the core of the preparation of the present invention is released gradually through this coating film into the outside of the preparation.

A core containing a drug, i.e., the present compound may be the present compound itself or a mixture, for example, of one or more of the following pharmaceutically acceptable additives (hereinafter, simply referred to as "additives") and the present compound in an amount of 1 to 99% by weight in the core.

1. Cellulose Derivatives

Crystalline cellulose, sodium carboxymethyl cellulose, alkyl celluloses such as methyl cellulose and ethyl cellulose, hydroxyalkyl celluloses such as hydroxypropyl cellulose or low substituted hydroxypropyl cellulose and hydroxypropylmethyl cellulose (2208, 2906, 2910), carboxymethyl cellulose, calcium carboxymethyl cellulose and sodium crosscarmellose.

2. Starches and Their Derivatives

Corn starch, potato starch, wheat starch, dextrin, pregelatinized starch, partly pregelatinized starch, sodium carboxymethyl starch, pullulan.

3. Saccharides and Sugar Alcohols

Lactose, sucrose, mannitol, xylitol, sorbitol.

4. Inorganic Materials

Kaolin, talc, magnesium stearate, titanium oxide, precipitated calcium carbonate, calcium hydrogen phosphate.

5. Plasticizers

Triethyl citrate, propylene glycol, triacetin, medium-chain fatty acid triglycerides.

Examples of an insoluble material employed in the present invention may include, for example, the following compounds. While the amount of such an insoluble material in a preparation may vary depending on the amount of the present compound, the degree of the release control to be desired, the insoluble material to be employed and other additives to be incorporated, it is usually 0.1 to 99% by weight, preferably 0.5 to 80% by weight, more preferably 1 to 50% by weight.

1. Higher Fatty Acids

Lauric acid, tridecanoic acid, myristic acid, pentadecanoic acid, palmitic acid, margaric acid, stearic acid, nonadecanoic acid, arachic acid, behenic acid, lignoceric acid, cerotinic acid, montanic acid.

2. Esters of Higher Fatty Acids with Alcohols

Glycerides of animal or vegetable derived fatty acids and mixtures thereof, hardened oil of such animal or vegetable derived glycerides (e.g., hydrogenated castor oil, hydrogenated rapeseed oil), glycerides of unsaturated fatty acids such as oleic acid, linoleic acid, linolenic acid, ricinoleic acid and the like as well as mixtures thereof.

3. Higher Alcohols

Pentadecanol, hexadecanol, heptadecanol, octadecanol, nonadecanol, eicosanol, wool alcohol, cholesterol.

4. Esters of Higher Alcohols with Fatty Acids

Cholesteryl palmitate, vegetable sterol palmitates.

5. Others

Ethyl cellulose, aminoalkyl methacrylate copolymer (Eudragit (Trade Mark) RS, RN100L, RN100, RSPM).

Any of such insoluble materials may be employed alone or in combination with each other.

The insoluble film-coated preparation according to the present invention may contain, as an instantaneous release part, the present compound itself or a mixture of the present compound and the above described additives.

It is also possible that the coating film of such an insoluble film-coated preparation contains the present compound, and one or more of the above described additives may also be contained for the purpose of controlling the release appropriately.

A more concrete example of the insoluble film-coated preparation according to the present invention may include, for example, a preparation obtained by coating a core containing the present compound (spherical plain granule) with at least one of aminoalkyl methacrylate copolymers such as Eudragit (Trade Mark) RS and ethyl cellulose, what is called, "sustained release granule".

The insoluble film-coated preparation according to the present invention can be produced in a conventional method, for example by spraying the above described insoluble material dissolved in an organic solvent such as ethanol or suspended in water onto a core containing the present compound using a device such as a fluidized layer granulating coater, centrifugal fluidized coater, aeration drying coater and the like. In the case of a waxy material amount in the above described insoluble materials, a core containing the present compound is coated with the melted insoluble material by a conventional method using a centrifugal fluidized coater, thereby accomplishing the production.

<2> Insoluble Medium Dispersion Preparation (Insoluble Matrix Preparation)

An insoluble medium dispersion preparation is one in which a drug (the present compound) is dispersed in a pharmaceutically acceptable medium (insoluble medium) which undergoes almost no dissolution in a fluid in a digestive tract. Such an insoluble medium dispersion preparation can control the release of the drug (the present compound) from the preparation by means of the enclosure of the drug in its insoluble medium.

Examples of the insoluble medium dispersion preparation according to the present invention may include GRADU-MET preparation and wax matrix preparation which contain the present compound as an active ingredient. The present compound is diffused through the insoluble film-coated layer and then released into the outside of the preparation.

Concrete examples of the insoluble medium may include, for example, those similar to the above described in soluble materials, and one or more of the insoluble media can be employed in the present invention.

While the amount of such an insoluble medium in the preparation may vary depending on the amount of the present compound, the degree of the release control to be desired, the insoluble medium to be employed and other additives to be incorporated, it is usually 1 to 99% by weight, preferably 3 to 80% by weight, more preferably 5 to 50% by weight.

Such an insoluble medium dispersion preparation may contain, as an instantaneous release part, the present compound itself or a mixture of the present compound and the above described additives.

It is also possible that the insoluble medium dispersion preparation can be coated with the insoluble material described above or with the soluble material that will be described later. The said insoluble material or soluble material described below may contain the present compound.

A more concrete example of the insoluble medium dispersion preparation according to the present invention may include, for example, a preparation containing a mixture whose essential components are the present compound and an insoluble medium such as a hydrogenated oil or a higher fatty acid, what is called, "wax matrix preparation". The mixture may also contain hydroxyalkyl celluloses such as hydroxypropylmethyl cellulose (HPMC) and hydroxypropyl cellulose (HPC), what is called, "wax-gel matrix preparation". This may be defined as an insoluble-soluble-medium-combination preparation, which is also encompassed by the present invention.

The insoluble medium dispersion preparation according to the present invention can be produced by a conventional method, for example, by subjecting a mixture of the present compound and the insoluble medium directly to the compaction into a tablet, by subjecting a mixture of the present compound and the insoluble medium to a granulation in a extrusion granulator to form a granular mass, which is occasionally compacted into a tablet, or by performing a series of processes such as mixing, kneading, shearing, heating and extrusion granulating using a device such as a fully intermeshing twin-screw compounding extruder having a kneading element in its screw shaft to obtain a granular mass, which is occasionally compacted into a tablet.

(2) Controlled Dissolution Oral Preparation

A controlled dissolution oral preparation is a preparation capable of controlling the release of a drug (the present compound) using a material which undergoes a dissolution in a fluid in a digestive tract, and examples thereof may be as follows.

<1> Soluble Film-coated Preparation

A soluble film-coated preparation has a core containing a drug (the present compound) coated with a pharmaceutically acceptable material which undergoes a dissolution in a fluid in a digestive tract (soluble material). Such a soluble film-coated preparation can control the release of the drug from the preparation depending on the dissolution or disintegration rate of the soluble material which forms a film-coated layer.

Concrete examples of the soluble film-coated preparation according to the present invention may include SPAN-THRU preparation, an enteric granule preparation, a mixture of enteric granules and gastric granules and REPE-TAB preparation containing the present compound as an active ingredient. The present compound is exposed and released as a result that the film-coated layer is dissolved gradually or disintegrated in a digestive tract.

A core containing the drug, i.e., the present compound may be the present compound itself or a mixture of one or more of the above described pharmaceutically acceptable additives in an amount of 1 to 99% by weight in the core and the present compound.

Examples of such a soluble material may include, for example, the following compounds. While the amount of such a soluble material in the preparation may vary depending on the amount of the present compound, the degree of the release control to be desired, the soluble material to be employed and other additives to be incorporated, it is usually 0.1 to 99% by weight, preferably 0.5 to 80% by weight, more preferably 1 to 50% by weight.

1. Cellulose Derivatives

Hydroxyalkyl celluloses such as hydroxypropyl cellulose, hydroxypropylmethyl cellulose and hydroxyethyl cellulose, methyl cellulose, carboxymethyl cellulose, carboxyethyl cellulose, hydroxypropylmethyl cellulose acetate succinate (AQOAT (Trade Mark) L, M, H), hydroxypropylmethyl cellulose phthalate (HP-55, HP-55S, HP-50), cellulose acetate phthalate, carboxymethylethyl cellulose.

2. Starches

Pregelatinized Starch, pregelatinized amylostarch, acid-treated starch, oxidized starch, dialdehyde starch, soluble starch, thin boiling starch, dextrin.

3. Dextrans

Dextran, dextran sulfate, carboxymethyl dextran.

4. Polysaccharides

Alginic acid, pectinic acid, arabic acid, alkali salt of arabic acid.

5. Latexes

Gum arabic, tragacanth, carrageenan.

6. Polypeptides

Polyglutamic acid, polyaspartic acid, polylysine, polyarginin.

7. Proteins

Gelatin, collagen, casein, albumin, globulin, gluten.

8. Acrylic Acid Derivatives

Polyacrylic acid, polymethacrylic acid, alkali salt of polymethacrylic acid, polymethacrylic acid-methacrylic acid copolymer, methacrylic acid copolymer (Eudragit, Trade Mark), L30D55, L100).

9. Vinyl Derivatives

Polyvinyl pyrrolidone, polyvinyl alcohol.

Any of such soluble materials may be employed alone or in combination with each other.

The soluble film-coated preparation according to the present invention may contain, as an instantaneous release part, the present compound itself or a mixture of the present compound and the above described additives.

It is also possible that the film-coated layer of such a soluble film-coated preparation contains the present compound, and one or more of the above described additives may also be contained for the purpose of controlling the release appropriately.

A more concrete example of the soluble film-coated preparation according to the present invention may include, for example, a preparation obtained by coating a core containing the present compound (spherical plain granule) with at least one of hydroxypropylmethylcellulose acetate succinate (AQOAT: Trade Mark) and methacrylic acid copolymers, what is called, "enteric release granule".

The soluble film-coated preparation according to the present invention can be produced in a conventional method, for example, by spraying the above described soluble material dissolved in an organic solvent such as ethanol or in water or suspended in water onto a core containing the present compound using a device such as a fluidized layer granulating coater, a centrifugal fluidized coater, an aeration drying coater and the like.

<2> Soluble Medium Dispersion Preparation (Soluble Matrix Preparation)

A soluble medium dispersion preparation is one in which a drug (the present compound) is dispersed in a pharmaceutically acceptable medium (soluble medium) which undergoes a dissolution in a fluid in a digestive tract. Such a soluble medium dispersion preparation can control the release of the drug from the preparation on the basis of the dissolution or disintegration rate of the soluble medium.

Examples of the soluble medium dispersion preparation according to the present invention may include SPACE-TAB preparation, a hydrophilic polymer matrix preparation, SPAN-TAB preparation (bilaminar tablet), LON-TAB preparation (double tablet, cored tablet), a triple tablet (inner core tablet) and the like. The present compound is released into the outside of the preparation as a result of the dissolution of the soluble medium from the outer layer followed by the exposure and dissolution of the present compound.

Examples of such a soluble medium may include, for example, those similar to the above described soluble materials, and one or more of the soluble media can be employed in the present invention.

While the amount of such a soluble medium in the preparation may vary depending on the amount of the present compound, the degree of the release control to be desired, the soluble medium to be employed and other additives to be incorporated, it is usually 1 to 99% by weight, preferably 3 to 80% by weight, more preferably 5 to 50% by weight.

Such a soluble medium dispersion preparation may contain, as an instantaneous release part, the present compound itself or a mixture of the present compound and the above described additives.

It is also possible that the soluble medium dispersion preparation can be coated with the above described insoluble material or with the above described soluble material. The above described insoluble material or soluble material may contain the present compound.

A more concrete example of the soluble medium dispersion preparation according to the present invention may include, for example, a preparation containing a mixture whose essential components are the present compound and a pharmaceutically acceptable hydrophilic polymer such as hydroxypropyl cellulose and hydroxypropyl cellulose, what is called "hydrophilic polymer matrix preparation".

The soluble medium dispersion preparation according to the present invention can be produced by a conventional method, for example, by subjecting a mixture of the present compound and the soluble medium directly to a compaction into a tablet, by subjecting a mixture of the present compound and the soluble medium to a granulation in a extrusion granulator to form a granular mass, which is occasionally compacted into a tablet, or by performing a series of processes such as mixing, kneading, shearing, heating and extrusion granulating using a device such as a fully intermeshing twin-screw compounding extruder having a kneading element in its screw shaft to obtain a granular mass, which is occasionally compacted into a tablet.

In the present invention, two or more of the insoluble film-coated preparations, insoluble medium dispersion preparations, soluble film-coated preparations and soluble medium dispersion preparations may be combined in an oral preparation.

The preparation of the present invention may contain, if necessary, an excipient such as lactose and corn starch, a lubricant such as magnesium stearate and talc, a binder such as polyvinyl alcohol and hydroxypropyl cellulose, a colorant such as red iron oxide, yellow iron oxide and titanium oxide, a flavor such as 1-menthol and orange extract, a surfactant such as an ester of sucrose with fatty acids and sodium lauryl sulfate, a stabilizer such as ascorbic acid and benzoic acid, any of which may be present in an amount of 0.1 to 90% by weight based on the preparation.

The preparation of the present invention can be used as a pharmaceutical for treating or preventing pollakiuria and urinary incontinence. The daily dose in an adult, as the present compound, may for example be 0.1 to 1000 mg/po, preferably 1 to 500 mg/po, and more preferably 10 to 300 mg/po. A higher or lower dose may be acceptable in some cases. The interval of the treatments may, for example, be 12 hours, 24 hours or 48 hours.

The preparation of the present invention is desirable to be administered in a unit dosage form. It may be in any of the dosage forms such as a powder, a capsule, a tablet, a sugar-coated tablet, a granule, a abstract, a microcapsule and the like, as a solid dosage unit.

Best Mode for Carrying out the Invention

Hereinafter, the present invention will be described in detail with reference to Examples, Comparative Example, and Test Examples. Needless to say, the present invention is not limited to the following Examples.

EXAMPLE 1

400 g of a sucrose-starch spherical granule (Non-pareil (Trade Mark) 101, FREUND INDUSTRIAL CO., LTD) of 24 to 32 mesh size was placed in a centrifugal fluidized coating granulator (FREUND INDUSTRIAL CO., LTD, CF-360), to which a powder mixture of 120 g of the present compound, 430 g of corn starch and 50 g of a low substituted hydroxypropyl cellulose was added in portions while spraying a 5% solution of polyvinyl alcohol to effect the granulation, followed by drying to obtain approximately 1000 g of spherical plane granules.

400 g of this spherical plane granules thus obtained were placed in the centrifugal fluidized coating granulator, and 600 mL of a solution including 120 g of Eudragit (Trade Mark) RS30D, 8 g of triethyl citrate and 12 g of talc in ethanol was sprayed to obtain the preparation of the present invention as a granule preparation (insoluble film-coated preparation).

EXAMPLE 2

400 g of the spherical plane granules produced in Example 1 were placed in the centrifugal fluidized coating granulator, and 600 mL of a solution including 90 g of Eudragit (Trade Mark) RS30D, 9 g of hydroxypropyl cellulose, 8 g of triethyl citrate and 12 g of talc in ethanol was sprayed to obtain the preparation of the present invention as a granule preparation (insoluble film-coated preparation).

EXAMPLE 3

400 g of the spherical plane granules produced in Example 1 were placed in the centrifugal fluidized coating granulator, and 1000 mL of a solution including 60 g of hydroxypropylmethyl cellulose acetate succinate (AQOAT (TradeMark) L), 6 g of triethyl citrate and 12 g of talc in a mixture of ethanol/water (6/4) was sprayed to obtain the preparation of the present invention as an enteric granule preparation (soluble film-coated preparation).

EXAMPLE 4

A powder mixture of 300 g of the present compound, 50 g of hydrogenated castor oil (product name: LUBRIWAX, FREUND INDUSTRIAL CO., LTD, hereinafter applied similarly) and 250 g of stearic acid (product name: Powdered stearic acid, NOF CORPORATION, hereinafter applied similarly) was placed in a kneader having a jacket in which a warm water at 75° C. was refluxed, and kneaded for 10 minutes. The kneaded mass was taken out and allowed to cool, sieved, and compacted under the pressure of 1000 kg/mold into tablets each weighing 240 mg and having the diameter of 8 mm, whereby obtaining the preparation of the present invention as a tablet (insoluble medium dispersion preparation).

EXAMPLE 5

500 g of the present compound, 270 g of hydrogenated castor oil and 230 g of sucrose fatty acid ester (product name: RYOTO SUGAR ESTER S-1670, MITSUBISHI-KAGAKU FOODS CORPORATION) were mixed and subjected to a fully intermeshing twin-screw compounding extruder having a kneading element in its screw shaft fitted with a 0.5 mm×15 holes-die (Model KEXN-30S20, KURIMOTO, LTD, hereinafter applied similarly, hereinafter simply referred to as the twin-screw compounding extruder), whose 2nd barrel temperature was set at 50° C., 3rd, 4th and 5th barrel temperature at 70° C. and die temperature at 70° C., and the powder mixture was fed at a rate of approximately 35 g per minute into the hopper and extruded at the screw rotation speed of 40 rpm. The molded articles thus extruded were sieved to obtain the preparation of the present invention as a granule preparation (insoluble medium dispersion preparation).

EXAMPLE 6

500 g of the present compound, 300 g of hydrogenated castor oil and 200 g of hydroxypropylmethyl cellulose 2906 were mixed and subjected to the twin-screw compounding extruder fitted with a 0.5 mm×15 holes-die, whose 2nd barrel temperature was set at 50° C., 3rd at 55° C., 4th at 60° C., 5th at 65° C. and die temperature at 70° C., and the powder mixture was fed at a rate of approximately 35 g per minute into the hopper and extruded at the screw rotation speed of 40 rpm. The molded articles thus extruded were sieved to obtain the preparation of the present invention as a granule preparation (insoluble-soluble-medium-combining dispersion preparation, wax-gel matrix).

EXAMPLE 7

500 g of the present compound, 200 g of hydrogenated castor oil, 150 g of stearic acid and 150 g of hydroxypropylmethyl cellulose 2906 were mixed and subjected to the procedure similar to that in Example 6 to obtain the preparation of the present invention as a granule preparation (insoluble medium/soluble medium-combining dispersion preparation, wax-gel matrix).

EXAMPLE 8

300 g of the present compound was mixed with 300 g of hydroxypropyl cellulose type M and the mixture was compacted under the pressure of 1000 kg/mold into tablets each weighing 240 mg and having the diameter of 8mm, there by obtaining the preparation of the present invention as a tablet preparation (soluble medium dispersion preparation).

EXAMPLE 9

300 g of the present compound was mixed with 250 g of hydroxypropyl cellulose type L and 50 g of crystalline cellulose, and the mixture was compacted under the pressure of 1000 kg/mold into tablets each weighing 240 mg and having the diameter of 8 mm, thereby obtaining the preparation of the present invention as a tablet preparation (soluble medium dispersion preparation)

EXAMPLE 10

10 g of the present compound, 5 g of stearic acid and 5 g of hydroxypropyl cellulose type M were placed on a mortar where they were mixed homogeneously, and filled as 240 mg aliquots into hard sized 1 capsules. The capsules were heated in an electric warmer at 70° C. for 10 minutes, taken out, allowed to cool at room temperature, thereby obtaining the preparation of the present invention as a capsule preparation (insoluble medium/soluble medium-combining dispersion preparation, gastric retained preparation).

Comparative Example 1 (Production of Conventional Preparation)

120 g of the present compound, 159 g of lactose and 66 g of corn starch were placed in a fluidized granulating drier and granulated while spraying a 8% solution of polyvinyl alcohol. To the mixture, magnesium stearate was added, and the mixture was compacted under the pressure of 700 kg/mold into tablets each weighing 120 mg and having the diameter of 7 mm, thereby obtaining a conventional preparation whose active ingredient is the present compound.

Test Example 1

The preparations of the present invention obtained in Examples 1 and 2 and the conventional preparation obtained in Comparative Example 1 were subjected to a dissolution test. The dissolution test was performed by proceeding with a sample corresponding to 80 mg of the present compound as directed in Method 2 under the 13th Japanese Pharmacopoeia at the paddle rotation speed of 50 rpm using 900 mL of purified water while measuring at the wavelength of 240 nm.

While the present compound was released rapidly from the conventional preparation as shown in FIG. 1, it was released slowly from the preparations of the present invention obtained in Examples 1 and 2, indicating a sufficient control of the release of the present compound from each preparation.

Test Example 2

The preparations of the present invention obtained in Examples 5, 6 and 7 and the conventional preparation obtained in Comparative Example 1 were subjected to a dissolution test. The dissolution test was performed by proceeding with a sample corresponding to 120 mg of the present compound as directed in Method 2 under the 13th Japanese Pharmacopoeia at the paddle rotation speed of 50 rpm using 900 mL of purified water while measuring at the wavelength of 240 nm.

While the present compound was dissolved rapidly from the conventional preparation as shown in FIG. 2, it was released slowly from the preparations of the present invention obtained in Examples 5, 6 and 7, indicating a sufficient control of the release of the present compound from each preparation.

Test Example 3

The preparations of the present invention obtained in Examples 8 and 9 and the conventional preparation obtained in Comparative Example 1 were subjected to a dissolution test. The dissolution test was performed by proceeding with a sample corresponding to 120 mg of the present compound as directed in Method 2 under the 13th Japanese Pharmacopoeia at the paddle rotation speed of 50 rpm using 900 mL of purified water while measuring at the wavelength of 240 nm.

While the present compound was released rapidly from the conventional preparation as shown in FIG. 3, it was released slowly from the preparations of the present invention obtained in Examples 8 and 9, indicating a sufficient control of the release of the present compound from each preparation.

Test Example 4

Each of the preparation of the present invention obtained in Example 6 and the conventional preparation obtained in Comparative Example 1 was given at a dose corresponding to 120 mg of the present compound orally together with 30 mL of water to each of three beagles (male, 8 to 12 kg) that were fastened overnight. Subsequently, the blood was taken at a certain time interval and the plasma levels of the present compound were measured by a high pressure liquid chromatography method (HPLC method).

As shown in FIG. 4, the preparation of the present invention obtained in Example 6 exhibited a sufficient control of the release of the present compound as reflected by the retarded peak of the plasma level and the absence of an excessively rapid increase in the initial plasma level when compared with the conventional preparation.

Figure 1:
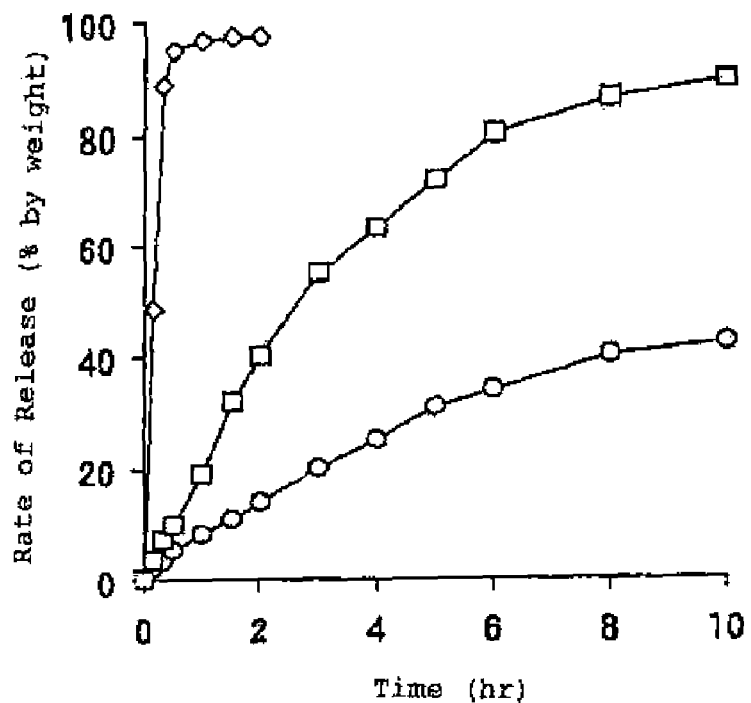
FIG. 1 shows the results of the dissolution test according to Test Example 1. The abscissa represents the time (hour), while the ordinate represents the ratio of release of the present compound (% by weight). A circle mark represents the release curve of the preparation of the present invention according to Example 1, a square mark represents the release curve of the preparation of the present invention according to Example 2, and a rhomb mark represents the release curve of the conventional preparation according to Comparative Example 1.
Figure 2:
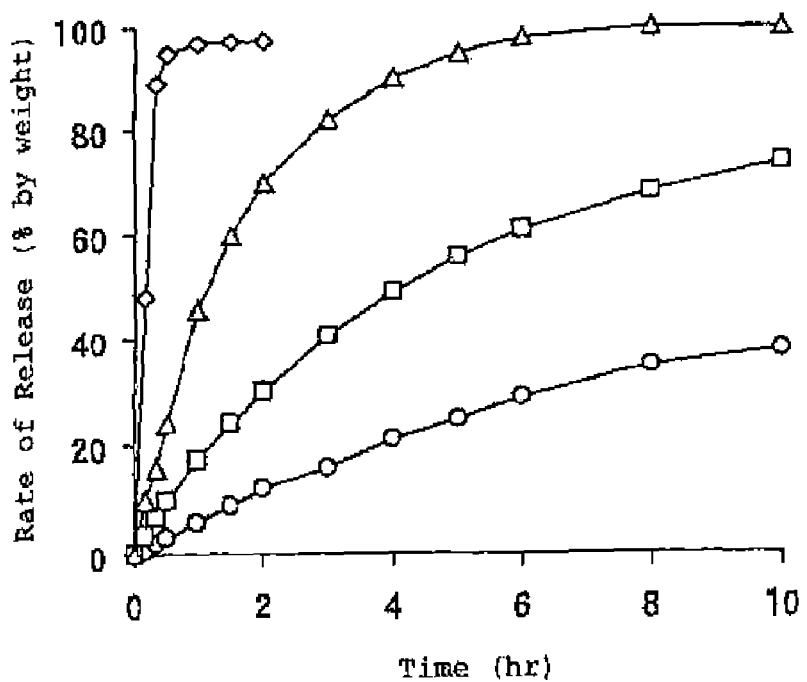
FIG. 2 shows the results of the dissolution test according to Test Example 2. The abscissa represents the time (hour), while the ordinate represents the ratio of release of the present compound (% by weight). A circle mark represents the release curve of the preparation of the present invention according to Example 5, a square mark represents the release curve of the preparation of the present invention according to Example 6, a triangle mark represents the release curve of the preparation of the present invention according to Example 7 and a rhomb mark represents the release curve of the conventional preparation according to Comparative Example 1.
Figure 3:
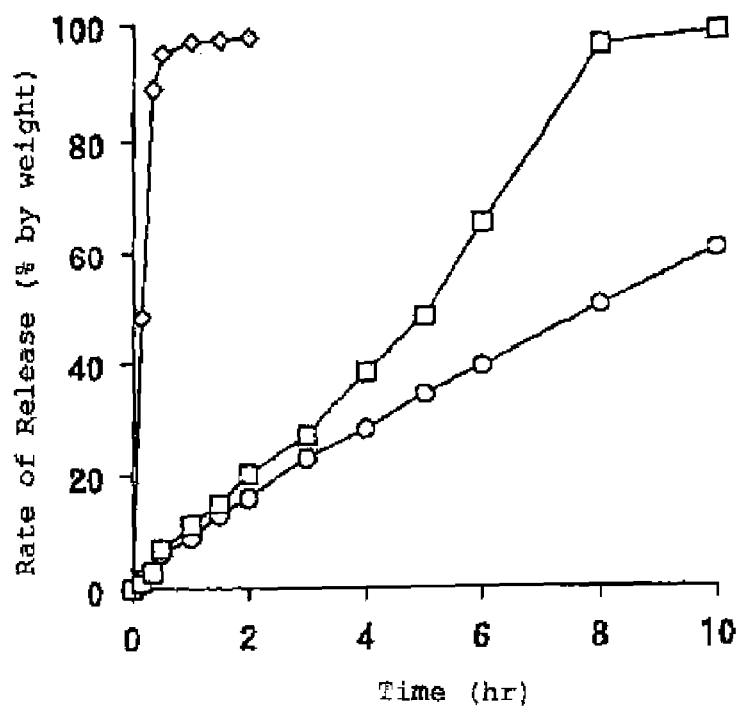
FIG. 3 shows the results of the dissolution test according to Test Example 3. The abscissa represents the time (hour), while the ordinate represents the ratio of release of the present compound (% by weight). A circle mark represents the release curve of the preparation of the present invention according to Example 8, a square mark represents the release curve of the preparation of the present invention according to Example 9, and a rhomb mark represents the release curve of the conventional preparation according to Comparative Example 1.
Figure 4:
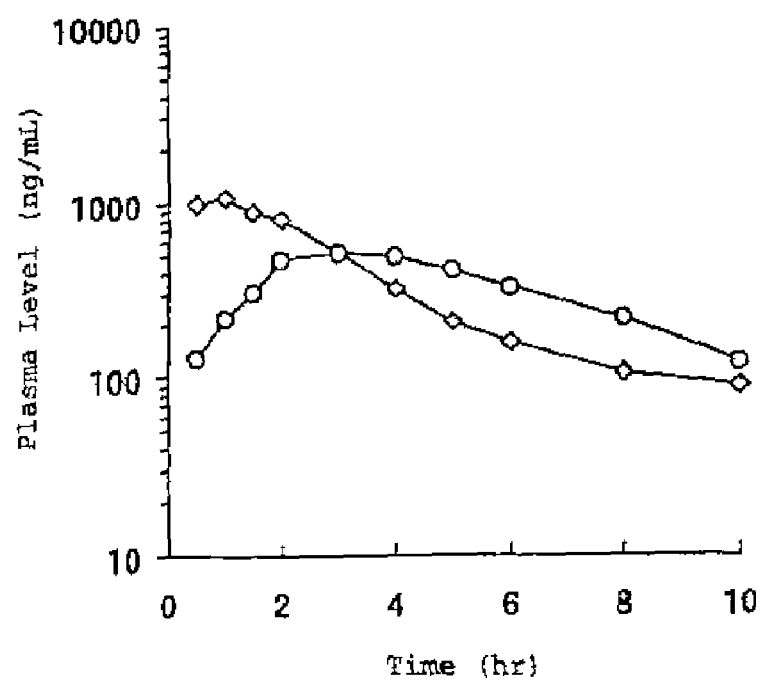
FIG. 4 shows the results of the in vivo test according to Test Example 4. The abscissa represents the time (hour), while the ordinate represents the plasma level of the present compound (ng/mL). A circle mark represents the change in the plasma level of the preparation of the present invention according to Example and a rhomb mark represents the change in the plasma level of the conventional preparation according to Comparative Example 1.

The invention claimed is:

1. A method of treating pollakiuria or urinary incontinence in a human subject comprising orally administering a controlled release oral preparation with a solid dosage form containing an effective amount of 2-amino-3-cyano-5-(2-fluorophenyl)-4-methylpyrrole as an active ingredient to the subject,
where the preparation exhibits a release ratio of the active ingredient of 0 to 70% by weight after 1 hour, 0 to 80% by weight after 2 hours, 5 to 95% by weight after 4 hours, 10 to 100% by weight after 8 hours, 20 to 100% by weight after 12 hours and 50 to 100% by weight after 24 hours in a dissolution test as directed in Method 2 under the $13^{th}$ Japanese Pharmacopoeia, wherein the preparation is placed in 900 mL of purified water and stirred with a paddle at a rotation speed of 50 rpm.

2. The method of claim 1, wherein the controlled release oral preparation is an insoluble film-coated preparation, an insoluble medium dispersion preparation, a soluble film-coated preparation or a soluble medium dispersion preparation or a combination of two or more of these oral preparations.

3. The method according to claim 2, wherein the insoluble film-coated preparation comprises a granule of which a core containing the active ingredient is coated with a pharmaceutically acceptable material consisting essentially of at least one of aminoalkyl methacrylate copolymers and ethyl cellulose.

4. The method according to claim 2, wherein the insoluble medium dispersion preparation comprises a composition of which the active ingredient is dispersed and enclosed in a pharmaceutically acceptable medium consisting essentially of an insoluble medium.

5. The method according to claim 4, wherein the insoluble medium is a hydrogenated oil or a higher fatty acid.

6. The method according to claim 4, wherein the medium further contains a hydroxyallkyl cellulose.

7. The method according to claim 5, wherein the hydrogenated oil is hydrogenated castor oil or hydrogenated rapeseed oil.

8. The method according to claim 5, wherein the higher fatty acid is stearic acid.

9. The method according to claim 6, wherein the hydroxyalkyl cellulose is hydroxypropylmethyl cellulose or hydroxypropyl cellulose.

10. The method according to claim 2, wherein the soluble film-coated preparation comprises a granule of which a core containing the active ingredient is coated with a pharmaceutically acceptable material consisting essentially of at least one of hydroxypropylmethyl cellulose acetate succinate and methacrylic acid copolymer.

11. The method according to claim 2, wherein the soluble medium dispersion preparation comprises a composition of which the active ingredient is dispersed and enclosed in a pharmaceutically acceptable medium consisting essentially of a soluble medium.

12. The method according to claim 11, wherein the soluble medium is a pharmaceutically acceptable hydrophilic polymer.

13. The method according to claim 12, wherein the pharmaceutically acceptable hydrophilic polymer is hydroxypropyl cellulose or hydroxypropylmethyl cellulose.

* * * * *